(12) United States Patent
Yoon et al.

(10) Patent No.: US 9,121,023 B2
(45) Date of Patent: Sep. 1, 2015

(54) POLYMERASE CHAIN REACTION PRODUCT-CLONING VECTOR SUITABLE TO ITS EASY PRODUCTION AND METHOD FOR PRODUCING THE SAME

(75) Inventors: Seongjun Yoon, Seoul (KR); SooYoun Jun, Seoul (KN); SangHyeon Kang, Seoul (KR)

(73) Assignee: INTRON BIOTECHNOLOGY, INC., Sungnam-Si (KR)

( * ) Notice: Subject to any disclaimer, the term of this patent is extended or adjusted under 35 U.S.C. 154(b) by 1277 days.

(21) Appl. No.: 12/740,003

(22) PCT Filed: Oct. 29, 2008

(86) PCT No.: PCT/KR2008/006378
§ 371 (c)(1),
(2), (4) Date: Apr. 27, 2010

(87) PCT Pub. No.: WO2009/057944
PCT Pub. Date: May 7, 2009

(65) Prior Publication Data
US 2010/0255570 A1     Oct. 7, 2010

(30) Foreign Application Priority Data
Oct. 30, 2007    (KR) .................. 10-2007-0109265

(51) Int. Cl.
*C12N 15/00*      (2006.01)
*C12N 15/64*      (2006.01)
*C12N 15/70*      (2006.01)

(52) U.S. Cl.
CPC ..................................... *C12N 15/70* (2013.01)

(58) Field of Classification Search
USPC .............................. 435/320.1, 29, 91.41, 471
See application file for complete search history.

(56) References Cited

U.S. PATENT DOCUMENTS 6,127,171 A * 10/2000 Slilaty et al. ................ 435/320.1

OTHER PUBLICATIONS

BLAST ® Basic Local Alignment Search Tool for SEQ ID No. 1. Last visited Aug. 1, 2013.*
Maneewannakul et al (1993, A T7 promoter-based vector system for protein engineering and expression; Score Search Results for U.S. Appl. No. 12/740,003 Result No. 1.*
Gabant P, Drèze PL, Van Reeth T, Szpirer J, Szpirer C. (1997) Bifunctional lacZ alpha-ccdB genes for selective cloning of PCR products. Biotechniques. 23(5): 938-941.
Holton TA, Graham MW. (1991) A simple and efficient method for direct cloning of PCR products using ddT-tailed vectors.Nucleic Acids Res. 19(5): 1156.
Hu G. (1993) DNA polymerase-catalyzed addition of nontemplated extra nucleotides to the 3' end of a DNA fragment. DNA Cell Biol. 12(8): 763-770.
Ichihara Y, Kurosawa Y. (1993) Construction of new T vectors for direct cloning of PCR products. Gene. 130(1): 153-154.
Kim DM, Kigawa T, Choi CY, Yokoyama S. (1996) A highly efficient cell-free protein synthesis system from *Escherichia coli* . Eur J Biochem. 239(3): 881-886.
Magnuson VL, Ally DS, Nylund SJ, Karanjawala ZE, Rayman JB, Knapp JI, Lowe AL, Ghosh S, Collins FS. (1996) Substrate nucleotide-determined non-templated addition of adenine by Taq DNA polymerase: implications for PCR-based genotyping and cloning. Biotechniques. 21(4): 700-709.
Marchuk D, Drumm M, Saulino A, Collins FS. (1991) Construction of T-vectors, a rapid and general system for direct cloning of unmodified PCR products. Nucleic Acids Res. 19(5): 1154.
Mead DA, Pey NK, Herrnstadt C, Marcil RA, Smith LM. (1991) A universal method for the direct cloning of PCR amplified nucleic acid. Biotechnology (NY). 9(7): 657-663.
Park HK, Zeng C. (2006) Construction of an XcmI-generated T vector bearing green fluorescent protein marker for direct cloning of PCR products. Anal Biochem. 360(1): 144-145.
Slilaty SN, Lebel S. (1998) Accurate insertional inactivation of lacZalpha: construction of pTrueBlue and M13TrueBlue cloning vectors. Gene. 213(1-2): 83-91.
Wang B, Liang H, Liu R, Li X, Sun B, Zhang R, Guo S, Guo G, Zhang J, Dai C. (2007) Construction of a restriction-endonuclease-Eam1105I-generated T-vector for high-throughput cloning and expression. Biotechnol Appl Biochem. 48(Pt 1): 29-33.
International Search Report issued on Apr. 27, 2009 for Application No. PCT/KR2008/006378 (WO/2009/057944), which was published on May 7, 2009.
International Preliminary Report on Patentability (including Written Opinion) issued on Jun. 1, 2010 for Application No. PCT/KR2008/006378 (WO/2009/057944), which was published on May 7, 2009.

* cited by examiner

*Primary Examiner* — Maria Leavitt
(74) *Attorney, Agent, or Firm* — Ballard Spahr LLP

(57) ABSTRACT

The present invention relates to a PCR product cloning vector applicable directly to the cloning of a PCR product. More precisely, the present invention relates to a PCR product cloning vector designed to be effective in use for blue/white colony selection and produced based on the restriction enzyme treatment process to generate non-complementary unpaired single overhang and a method for producing the same. According to the method of the present invention, the PCR product cloning vector designed to be advantageous for blue/white cloning selection can be produced with improved efficiency compared with the convention method.

4 Claims, 4 Drawing Sheets

Single alpha-peptide system

POLYMERASE CHAIN REACTION PRODUCT-CLONING VECTOR SUITABLE TO ITS EASY PRODUCTION AND METHOD FOR PRODUCING THE SAME

CROSS-REFERENCE TO RELATED APPLICATIONS

The present application is a National Phase Application of International Application No. PCT/KR2008/006378 filed Oct. 29, 2008, which claims priority to Korean Patent Application No. 10-2007-0109265 filed Oct. 30, 2007, which applications are incorporated in their entireties herein by this reference.

TECHNICAL FIELD

The present invention relates to a polymerase chain reaction (PCR) product cloning vector, more precisely a PCR product cloning vector designed to confirm its cloning by blue/white colony selection and synthesized by the production method using a restriction enzyme forming non-complementary unpaired single overhang, and a preparation method of the same.

BACKGROUND ART

In molecular biology experiments, a gene carrier called "vector" is used for convenience in dealing with genes and for long term preservation. This vector is basically circular double-stranded DNA (dsDNA). According to the elements and use, the vector is classified into cloning vector, transcription vector and translation vector, etc.

When a gene is inserted into a vector, it is called "cloning". Various methods have been developed for cloning. Among them, the most common method is to use restriction enzyme treatment and ligation. In restriction enzyme treatment, restriction enzymes digest DNA into DNA fragments. In ligation, a ligase can insert the purified DNA fragment generated by precedent restriction enzyme treatment into a vector.

In this method, restriction enzymes digest DNA in the specific site which an experimenter wants to cut and ligase mediates ligation between ends of DNA fragments. In this method, DNA fragment is first prepared by digesting DNA using restriction enzymes and the vector is also digested by the same restriction enzyme to make DNA cloning site (sometimes, DNA and a vector are digested with different enzymes, which is not general, though). When DNA is digested with a restriction enzyme, a specific site of DNA cut by the restriction enzyme is called "restriction enzyme recognition sequence". This restriction enzyme recognition sequence is also called "restriction enzyme recognition site" and in some cases it is understood as a restriction enzyme catalytic site (cleavage site). This restriction enzyme recognition sequence differs among restriction enzymes. So, an experimenter needs to select a proper restriction enzyme for his experiment. DNA digested with a restriction enzyme has sticky-end or blunt-end.

To prepare a DNA fragment to be inserted into a vector, DNA is treated with restriction enzymes. The DNA fragment is then purified from restriction enzyme treated reaction mixture. To prepare a vector fragment, a vector is also treated with restriction enzymes and as a result a vector fragment having DNA cloning site is prepared (linearized structure). This vector fragment is also purified from restriction enzyme treated reaction mixture. The purification of DNA fragment and vector fragment from restriction enzyme treated reaction mixture can be performed by using a commercial DNA purification kit. And this purification can be performed easily by those in the art, so that precise description is not given herein.

To ligate a purified DNA fragment and a purified vector fragment, these two fragments are added to ligation buffer at a proper molar ratio, to which ligase is added, followed by inducing ligase reaction (ligation among DNA fragments). Accordingly, the end of DNA fragment is linked to the end of linearized vector fragment, resulting in a circular plasmid, suggesting the completion of cloning. The plasmid herein indicates the circular double-stranded DNA.

It is not easy and inefficient to separate and purify a cloning product alone from ligation reaction mixture to use it for the next step of experiment. Even if it is successfully separated and purified, the amount is not sufficient for the next step. Therefore, in most cases, transformation using *Escherichia coli* is performed to obtain enough amount of a cloning product. In general, transformation is performed by using heat-shock method. Sometimes, transformation using electroporation is performed but to transform *E. coli* using a small sized plasmid, heat-shock method is enough working. Transformation by heat-shock is performed as follows. 10 μl of ligation mixture was added to 100 μl of *E. coli* solution in which cell membranes of the cells are loosened by treating calcium chloride (generally called 'competent cell'). The mixture is then left in ice for 30 minutes to let the cloning product to be adhered on the surface of *E. coli*. 30 minutes later, the mixture is transferred quickly to a 42° C. bath and left therein for 1 minute. This is called as 'heat-shock'. At this time, the cloning product penetrates into *E. coli*. After heat-shock, the mixture is transferred again into ice quickly and left therein for 1 minute. After 1 minute of staying in ice, the mixture is taken out of ice, to which 800 μl of a proper culture medium is added. Generally, LB medium (trypton, 10 g/L; yeast extract, 5 g/L; sodium chloride, 10 g/L) is used in transformation. After adding a culture medium, the reaction mixture is incubated at 37° C. for one hour. During this incubation, cell membranes damaged by calcium chloride treatment become recovered. After one hour of incubation, the mixture is spread on a plate medium containing a proper antibiotic, followed by culture in an incubator until proper sized colonies are formed. At this time, a colony indicates *E. coli* cells proliferated from one *E. coli* cell. When colonies are formed big enough, it is considered that transformants are generated. And, the transformant is transferred into a liquid medium (generally LB medium), followed by further culture. From the cultured cells, enough amount of plasmid can be obtained.

To increase convenience and efficiency of cloning, diverse methods have been developed by modifying the conventional cloning method composed of a restriction enzyme treatment and ligation. One example is the method of using a specially designed vector capable of accepting a PCR-amplified product, which is related to the present invention.

PCR is a reaction using DNA polymerase, which produces massive amount of DNA amplicons from template DNA. PCR is a well-known, general technique used for biological study and for disease diagnosis. Cloning of such PCR product can also be achieved by the cloning method using a restriction enzyme and ligase as explained hereinbefore. However, to do so, an amplified PCR product has to contain a restriction enzyme recognition sequence. To introduce a restriction enzyme recognition sequence into a PCR product, a specifically designed PCR primer is required. The primer has to contain 6-10 nucleotides corresponding to a restriction enzyme recognition sequence selected by an experimenter in addition to the nucleotide sequence (priming sequence) binding to a template. A PCR product obtained by using a primer containing a selected restriction enzyme recognition sequence cannot be directly linked to a vector fragment because the cloning site is not exposed. So, after digesting a PCR product by a corresponding restriction enzyme and purification of the restriction enzyme treated PCR product, insertion into a vector fragment is performed.

However, the above method uses a PCR product as a cloning target instead of general DNA, which is the only difference from the conventional cloning method composed of a restriction enzyme treatment and ligation. Therefore, the method does not provide a special effect or convenience. Besides, a primer specially designed as the above contains additional nucleotides in addition to annealing sequence binding to nucleotide sequence of a target gene, suggesting that efficiency in template specific primer annealing decreases. A PCR product generated by the method contains restriction enzyme recognition sequences in both ends, suggesting that digestion efficiency by a restriction enzyme decreases. In general, when a restriction enzyme recognition sequence is located in terminal region of DNA molecule, digestion efficiency is lower than when it is located in the middle.

Therefore, many researchers tried to develop more simple method for cloning of PCR product and to improve efficiency of restriction enzyme treatment to a PCR product. As a result, they proposed the method in which restriction enzyme treatment step that has been always necessary according to the conventional cloning method is omitted. As an example, PCR product cloning method using topoisomerase I or a vector designed to be suitable for direct cloning of PCR product without restriction enzyme treatment was proposed.

The PCR product cloning method of the present invention is related to the latter, which is direct cloning of PCR product into a linearized vector fragment without restriction enzyme treatment. The linearized vector used for direct PCR product cloning without using a restriction enzyme is largely divided into two groups according to the type of terminal region of the PCR product used in cloning. One is the linearized vector fragment designed suitable for direct cloning of PCR product having blunt ends. The other is the linearized vector fragment designed suitable for direct cloning of PCR product having non-complementary unpaired single overhang in the end of only one chain of double strands.

A PCR product is a double-stranded DNA having a linearized structure in which two strands are complementarily combined. In general, the end form of PCR product is determined by DNA polymerase used in its amplification. That is, a PCR product can have either blunt ends or non-complementary unpaired single overhang ends according to the kind of DNA polymerase used. So, an experimenter can choose proper DNA polymerase considering the purpose of the experiment. For example, when Taq DNA polymerase frequently used for PCR as a thermophilic enzyme or Tth DNA polymerase is used, a unique PCR product having non-complementary unpaired single overhang at both 3'-ends is produced by template-independent addition. The nucleotide residue forming the non-complementary unpaired single overhang can be any of single deoxyadenosine monophosphate residue (dAMP; indicated as 'A' herein for convenience), single deoxythymidine monophosphate residue (dTMP; indicated as 'T' herein for convenience), single deoxyguanosine monophosphate (dGMP; indicated as 'G' herein for convenience), and single deoxycytidine monophosphate residue (dCMP; indicated as 'C' herein for convenience). Among them, the most frequent occurrence is A-overhang. It was reported that the type of overhang is determined by primer sequence (Hu, DNA Cell Biol. 12: 763, 1993; Magnuson et al., BioTechniques 21: 700, 1996).

As explained hereinbefore, a specially designed vector (mentioned as a vector for convenience, but exactly speaking it is a vector fragment) is required for direct cloning of a PCR product having blunt ends or overhang ends.

Basically, cloning of a PCR product having blunt ends (or even if a PCR product had overhang ends but the overhang ends have been eliminated by the treatment of nuclease, it is included in the group of PCR products having blunt ends) can be achieved only with a linearized vector fragment having blunt ends. So, this kind of cloning is theoretically simple. To prepare a linearized vector fragment having blunt ends, a restriction enzyme such as EcoR V, Dra I, or Hinc II can be used. A PCR product having blunt ends can be linked to a linearized vector fragment having blunt ends by ligase under the conventional DNA ligation conditions. However, according to this method, coupling between vector fragments or intra-molecularar circulization of vector fragments is dominant over real cloning, suggesting that cloning efficiency is reduced.

On the other hand, the production of a vector fragment for the direct cloning of such a PCR product having unpaired single overhang and the cloning of the same are rather complicated. For direct cloning of a PCR product having overhang ends, a linearized vector fragment having overhang ends matching to the overhang ends of a PCR product (complementary binding) is required. So, the overhang of a linearized vector fragment has to be located in the opposite strand to the overhang of a PCR product for complementary binding. To help understand the relative location of overhang, a schematic diagram illustrating the relative locations of terminal overhangs of a vector fragment and a PCR product is presented in FIG. 1. In PCR products, A-overhang is most frequently observed. So, T-overhang is most appropriate as terminal overhang of a vector fragment, but not necessarily limited thereto. Instead, a vector fragment can have any of A-overhang, C-overhang, and G-overhang. It is general to unite two overhangs of both ends of a vector fragment, but not always limited thereto. However, since A-overhang is most frequently observed in end of a PCR product, it is preferred for a vector fragment to have T-overhangs in both ends for complementary binding. Therefore, description hereinafter is focused on the vector fragment having T-overhang. It is only for convenience in explanation but cannot limit the present invention thereto.

Linearized vector fragments having overhang ends can be produced by two different methods. Both use a circular parental vector (indicating a starting vector for the production of a vector fragment, and in this invention, it is called as 'parental vector'). One of the methods is the method using restriction enzymes capable of producing blunt ends. In this method, a circular parental vector is digested with a restriction enzyme capable of producing blunt ends. Then, the prepared linearized vector fragment having blunt ends is purified. In the next stage, an overhang is added to the blunt ends of the linearized vector fragment, followed by purification again. At this time, a restriction enzyme capable of producing blunt ends is exemplified by EcoR V, Dra I, and Hinc II. To form an additional overhang, Taq DNA polymerase (Marchunk, D. et al., Nucleic Acid Res. 19: 1154. 1991) or terminal deoxynucleotidyl transferase (Holton, T. A. et al., Nucleic Acid Res. 19: 1156, 1991) is used in the presence of excess amount of $Mg^{2+}$. According to this method, efficiency of addition of overhang to the end of a vector fragment depends on the activity of the selected modifying enzyme. So, there is still a high chance for a vector fragment to remain as an incomplete vector fragment that does not contain an additional overhang. Such an incomplete vector fragment without having an overhang can form intra-molecular circulizated molecule (self-ligation) during ligation and cannot be used for cloning. Therefore, this causes the decrease of cloning efficiency.

The other method is the method of using restriction enzymes capable of producing a linearized vector fragment having overhang ends without any additional treatment (Yoshikazu, I. et al., Gene 130: 152, 1993; David A. M., et al., Bio/Technology 9: 65, 1991). A restriction enzyme used at this time is exemplified by Ahd I, BciV I, Bfi I, Bfu I, Bmr I, BspOV I, Dri I, Eam1105 I, EclHK I, Hph I, Mbo I, Mnl I, Ncu I, NruG I, Taa I, Tsp4C I and Xcm I. Particularly, a parental vector having 1-2 restriction enzyme recognition sequences capable of being used for producing overhang ends directly is treated with a proper restriction enzyme, and as a result, a vector fragment having non-complementary unpaired single overhang at the end is prepared. It is not preferred but is possible for a parental vector to have several restriction enzyme recognition sequences capable of being used for producing overhang ends in several different regions. If that is the case, effective restriction enzyme recognition sequences are two sequences that are located outmost from the DNA fragment cut out of the parental vector.

To perform the cloning of a PCR product having overhang ends into a linearized vector fragment having overhang ends, these two fragments and ligase are added to ligation buffer, followed by ligation. To obtain massive cloning products after ligation, E. coli is transformed with the ligation mixture. At this time, other plasmids effective in transformation can be included in addition to the cloned plasmid in ligation mixture. The parental vector used for the production of a linearized vector fragment having overhang ends or the recirculized plasmid of the incompletely digested parental vector (one of the two restriction enzyme recognition sequences is digested but recirculized as a parental vector from ligation) can be included, although the amount is small. It is theoretically possible to eliminate these vectors completely by intensive separation and purification after restriction enzyme treatment. However, such complete elimination is not easy and some of the vectors are included generally. When a parental vector is digested with a restriction enzyme to produce a linearized vector fragment having overhang ends, a released DNA fragment is too small. So, on agarose gel electrophoresis, difference in mobility of each the vector digested completely and the vector digested incompletely is not so great. Thus, no matter how badly want to separate and purify a completely digested vector fragment alone using gel-extraction, an incompletely digested vector fragment or non-digested parental vector can still be included, which has to be overcome.

For the conventional transformation, a selection medium containing antibiotics is generally used. So, E. coli that does not have such a plasmid containing an antibiotic resistant gene cannot be growing on that medium. E. coli that has not been transformed with the plasmid containing an antibiotic resistant gene is fundamentally eliminated from the selection. Even if such E. coli that is not transformed with the plasmid containing an antibiotic resistant gene in the selection medium is eliminated first, E. coli transformed with a recirculized plasmid generated from a incompletely digested parental vector fragment, a parental vector itself, or a cloning product can have the plasmid containing an antibiotic resistant gene, suggesting that the E. coli transformed with these plasmids can grow in the selection medium containing antibiotics. So, the selection of the transformant having a cloning product using antibiotics is not possible.

To isolate only the transformant having a cloning product, blue/white colony selection method is proposed. The blue/white colony selection method uses a special medium and E. coli transformed with a proper cloning product can be determined by its apparent color. Accordingly, it is possible to distinguish a colony having a plasmid successfully cloned from a colony which does not. E. coli used for blue/white colony selection is genetically modified to fit for blue/white selection method, which is well known to those in the art, so the explanation thereof is omitted herein. If E. coli does not have a plasmid or has a plasmid but not expressing alpha-peptide, a white colony is formed in blue/white colony selection. E. coli which does not have any plasmid cannot be growing in the selection medium containing antibiotics because it does not contain any antibiotic resistant gene. So, there is no need to worry about such E. coli. In general, a transformant having a recirculized plasmid generated from an incompletely digested parental vector fragment or a parental vector appears as a blue colony in blue/white colony selection, while a transformant having a cloning product appears as a white colony in blue/white colony selection. That is, E. coli having the unproper cloning product can express alpha-peptide and appears a blue colony. If E. coli is transformed with a proper cloning product, E. coli cannot express alpha-peptide and appears as a white colony.

Blue/white colony selection is based on the action of alpha-peptide. So a plasmid applicable for blue/white colony selection has to contain a gene encoding alpha-peptide. Also, factors and sequences necessary for the expression of alpha-peptide (corresponding promoter, etc) have to be included in the plasmid as well. Alpha-peptide is N-terminal region of beta-galactosidase and the gene encoding alpha-peptide is represented by SEQ. ID. NO: 1. Alpha-peptide is an enzyme converting 5-Bromo-4-chloro-3-indolyl β-D-galatopyranoside (X-Gal) into a blue-colored material. To perform blue/white colony selection, alpha-peptide has to be expressed from the plasmid used for the transformation. To do so, isopropyl β-D-1-thiogalactopyranoside (IPTG) is added to the medium as expression inducer.

Therefore, alpha-peptide gene sequence has to be included in a plasmid used for the transformation for blue/white colony selection and the alpha-peptide sequence included in plasmid is provided by a cloning vector used in construction of the plasmid. Some parts of alpha-peptide sequence can be modified. In many commercial cloning vectors, some parts of alpha-peptide sequence have been modified from an original sequence to introduce cloning region within the alpha-peptide gene. Such modification is of course limited and has to be confirmed by experiments. Examples of acceptable modification have been known, based on which diverse modification attempts in the sequence have been made. Relevant references are easily obtained by those in the art, so the precise explanation is omitted in this invention.

In order for a transformant having a recirculized plasmid generated from an incompletely digested parental vector fragment or a parental vector to form a blue colony, alpha-peptide has to be expressed from these plasmids. To do so, reading frame of alpha-peptide is composed of a contiguous and non-overlapping set of three-nucleotide codons. Even if a part of alpha-peptide sequence is modified, complete open reading frame has to be in-frame. In order for a transformant to form a white colony, the cloned gene is located in the inside of alpha-peptide gene. That is, the cloning has to be able to knockout the alpha-peptide gene. In general, when a big size gene is inserted within alpha-peptide gene, alpha-peptide gene is knockout. So, blue/white colony selection explained above has been widely used to isolate colonies having cloning products.

As explained hereinbefore, distinguishment of a parental vector and an incompletely digested parental vector fragment from a completely digested parental vector is very difficult. They are usually mixed. Precisely, a transformant having a parental vector, a transformant having a recirculized plasmid, and a transformant having a cloning product can be distinguished in blue/white colony selection, so it causes no big confusion. Significant problem caused by inefficiency of a restriction enzyme is that the amount of effective vector fragments obtainable from equal amount of a parental vector is much less, resulting in inefficiency in production process. If cloning is performed with such vector fragments including a parental vector or an incompletely digested parental vector, which means as the amount of effective vector fragment used for real cloning becomes less, cloning efficiency will be decreased. Even if it is so difficult to distinguish a completely digested parental vector fragment alone from an incompletely digested parental vector fragment or a parental vector, the problem can be minimized by maximizing efficiency of a restriction enzyme during the production of a vector fragment. If the distance between restriction enzyme recognition sequences is too close, the functions of those restriction enzymes are interrupted, resulting in incomplete digestion. This problem is only caused by too close distance between restriction enzyme recognition sequences in the parental vector used for vector fragment production, so it can be improved by extending the distance. And the extension of the distance between restriction enzyme recognition sequences in the parental vector can be achieved by inserting an additional gene in between the restriction enzyme recognition sequences. The insertion of an additional gene can increase efficiency of a restriction enzyme and facilitates separation and recovery of products by taking advantage of difference in size of products after the treatment of restriction enzyme. However, such insertion of an additional gene in between the restriction enzyme recognition sequences present within the alpha-peptide gene may knockout alpha-peptide gene necessary for blue/white colony selection. This is consistent with that a transformant transformed with a cloning product having gene insertion in alpha-peptide sequence appears as a white colony in blue/white colony selection. That is, the insertion of an additional gene in between the restriction enzyme recognition sequences brings another problem of making selection of colonies having a parental vector or a recirculized parental vector by color impossible because all transformants having a cloning product and a parental vector appear as white colonies in blue/white colony selection.

The present inventors completed this invention by establishing a method for producing a PCR product cloning vector fragment which can overcome the problems of the conventional method such as inefficient digestion in restriction enzyme treatment and difficulty in separation of a restriction enzyme treated vector fragment and at the same time facilitates distinguishment of each transformant respectively transformed with a parental vector and a recirculized plasmid generated from an incompletely digested parental vector fragment by making them presented as blue colonies in blue/white colony selection.

DISCLOSURE

Technical Problem

It is an object of the present invention to overcome the problems including technical problems of the prior art. That is, the present invention provides a method that can overcome the problems of PCR product cloning vector production, such as inefficient digestion frequently observed during the restriction enzyme treatment performed for generating a linearized vector fragment having overhangs and difficulty in separation of a restriction enzyme treated vector fragment and facilitates selection of the transformant having a cloning product by blue/white colony selection even if a transformant is generated by transformation with a contaminated parental vector or a recirculized plasmid generated from an incompletely digested parental vector fragment.

It is another object of the present invention to provide a PCR product cloning vector fragment having non-complementary unpaired single overhang ends facilitating blue/white colony selection based on the method of the present invention.

Technical Solution

In the conventional method of producing a PCR product cloning vector, in the step of treating a parental vector with a restriction enzyme to form a linearized vector fragment having overhang, inefficiency in digestion and difficulty in separation of a generated vector fragment have always been problems. The present invention provides a method to overcome the above problems. In addition, the present invention provides a method that facilitates the distinguishment of a transformant having a parental vector or a recirculized plasmid generated from an incompletely digested parental vector fragment by making it presented as blue colonies in blue/white colony selection.

Therefore, in order to increase digesting efficiency of a restriction enzyme used for generating a vector fragment having non-complementary unpaired single overhang ends from a parental vector used for the production of a PCR product cloning vector, to improve separation of a digested product, and to present a transformant having a contaminated parental vector or a recirculized plasmid generated from an incompletely digested parental vector fragment as a blue colony in blue/white colony selection, the present invention provides a production method of a PCR product cloning vector comprising the following steps:

1) locating the total sequence of alpha-peptide gene represented by SEQ. ID. NO: 1 and a promoter sequence necessary for the expression of the gene in a parental vector;

2) introducing 2-5 restriction enzyme recognition sequences within the alpha-peptide gene sequence of step 1) in order to use for generating non-complementary unpaired single overhang ends therein; and 3) inserting another alpha-peptide gene sequence and a promoter sequence necessary for the expression of the additionally added alpha-peptide gene in between the any two restriction enzyme recognition sequences inserted for using in generating the non-complementary unpaired single overhang ends of step 2), resulting in a specially designed final vector to have two alpha-peptide sequences.

The production method of a PCR product cloning vector of the present invention is described in more detail in Example 1 and Example 2.

In the parental vector of the present invention, another alpha-peptide sequence is inserted within the pre-inserted alpha-peptide sequence, which means the pre-inserted alpha-peptide sequence is divided into two parts by another alpha-peptide sequence. This is explained in the schematic diagram of FIG. 2. And the sequence composed like this is represented by SEQ. ID. NO: 4.

Except that, the PCR product cloning vector fragment of the present invention has the same characteristics with the conventional PCR product cloning vectors as follows.

The PCR product cloning vector has a linear DNA structure in which two nucleotide strands are linked with having both ends. Both ends have non-complementary unpaired single overhang in one strand and such non-complementary unpaired single overhang is located in different strands. The restriction enzyme recognition sequence forming the overhang exists in outer alpha-peptide gene sequence, so the end having an overhang is generated as a part of the outer alpha-peptide sequence is cut off. The inner alpha-peptide is completely eliminated by treatment with a restriction enzyme. As explained hereinbefore, the alpha-peptide gene sequence can be partially modified within a limited range. No matter what modification is applied, as long as the original characteristics of alpha-peptide is not changed, the alpha-peptide can be used in this invention, which means the invention can achieve its goal without being affected by the modified alpha-peptide sequence.

As explained hereinbefore, the PCR product cloning vector fragment having overhang ends can be prepared by two different methods. These methods are all started with a circular parental vector. The first method to produce a vector fragment having both ends containing an overhang comprises the following steps; treating a parental vector to produce a vector fragment having blunt ends with a restriction enzyme; separating the linearized vector fragments from the intact parental vector; and generating a secondary overhang by using an enzyme capable of producing an overhang at the blunt ends of both ends. The second method is to let the restriction enzyme recognition site itself produce an overhang right on the site.

According to the first method to produce an overhang at the blunt ends by using a parental vector to produce a PCR product cloning vector, one restriction enzyme recognition sequence can digest only one site. So, as described in this invention, it cannot cooperate with the method of the present invention to arrange two alpha-peptide sequences in a parental vector.

However, the method of the present invention is effective for the second method to produce a PCR product cloning vector by using a restriction enzyme capable of generating non-complementary unpaired single overhang. Many researchers are well aware of the necessity of insertion of an additional sequence in between the two restriction enzyme recognition sequences in order to improve the efficiency of restriction enzyme treatment and to increase convenience in separation and purification of the restriction enzyme treated vector fragment. However, such insertion of an additional sequence in between the two restriction enzyme recognition sequences results in knockout of alpha-peptide gene necessary for blue/white colony selection. So, the above method is not effectively applied in reality. The present inventors overcome the problem by inserting another alpha-peptide sequence as an additional sequence within the pre-inserted alpha-peptide sequence included in a parental vector, the staring vector of a PCR product cloning vector.

The parental vector necessary for the production of a PCR product cloning vector having the mentioned characteristics has the structure of FIG. 4.

In a preferred embodiment of the present invention, it was proved that the method using the PCR product cloning vector fragment of the present invention facilitated more efficient cloning than the conventional method.

The method of the present invention also solved the problem of the conventional method. That is, according to the method of the present invention, even if a long gene sequence is inserted in between restriction enzyme recognition sequences selected for generating overhangs in a parental vector to increase efficiency of vector fragment production, a transformant having the parental vector appears as a blue colony. So, the transformant not having a cloning product, which sometimes may appear as a white colony in the conventional method, always appears as a blue colony, making selection easy in blue/white colony selection. The above phenomenon was also confirmed by that the ratio of colonies having a cloning product in colonies expressed as white remained unchanged.

Therefore, when the PCR product cloning vector fragment prepared by the method of the present invention is used, cloning efficiency is increased and effective colonies having a cloning product can be selected by blue/white colony selection by selecting only white colonies.

Advantageous Effect

The present invention provides an efficient method for producing a PCR product cloning vector. As described in this invention, by locating two alpha-peptide sequences in a parental vector, the distance between the two restriction enzyme recognition sequences used for forming non-complementary unpaired single overhangs becomes far, resulting in improvement of efficiency in the restriction enzyme treatment. In addition, the size of a vector fragment generated by the treatment of restriction enzyme changes significantly, compared with that of the parental vector or incompletely digested parental vector, suggesting that separation/purification of the restriction enzyme treated vector fragment becomes easy. A transformant generated by transformation with the parental vector of the present invention or a recirculized plasmid generated from an incompletely digested parental vector appears as a blue colony due to inner alpha-peptide sequence arranged in the inside of another outer alpha-peptide sequence, so that it eliminates the aware of contamination with a parental vector or a incompletely digested parental vector fragment. Therefore, the present invention can be effectively used for cloning necessary for the studies on functions of a newly found gene and application studies of the conventional genes.

DESCRIPTION OF DRAWINGS

The application of the preferred embodiments of the present invention is best understood with reference to the accompanying drawings, wherein:

In FIG. 5, N indicates any of the following four nucleotides, A, C, G, and T. The nucleotide marked as N has to be bound with another nucleotide strand by a complementary base pair.

BEST MODE

Figure 1:
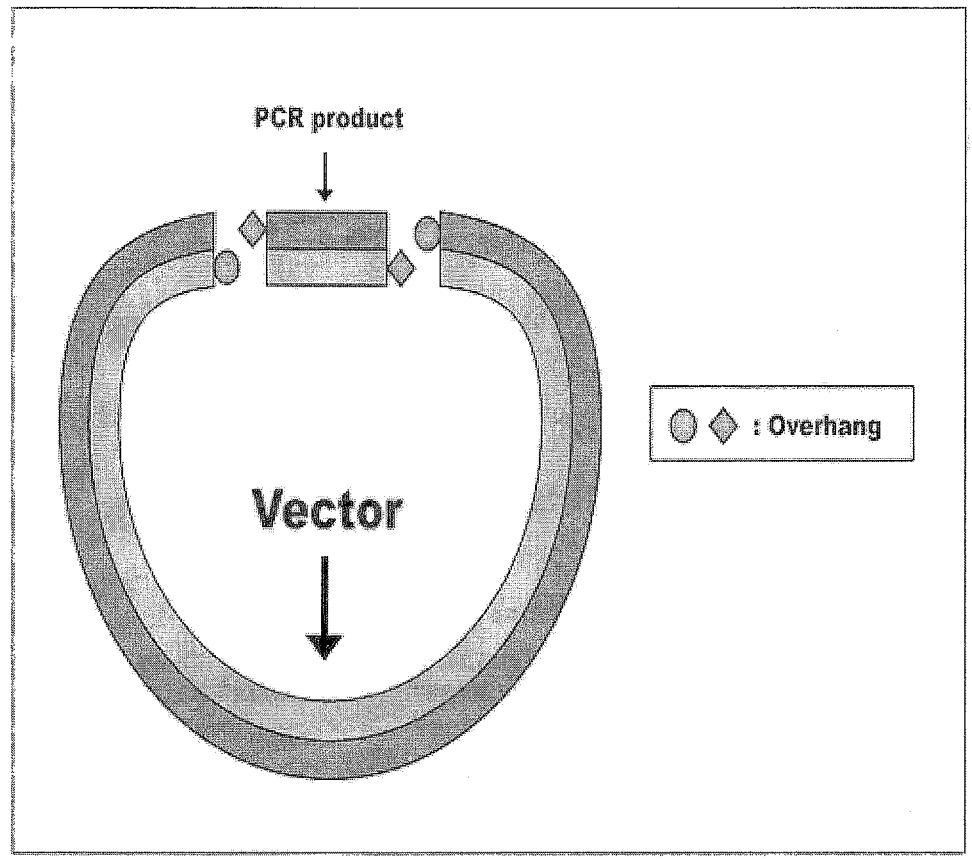
FIG. 1 is a schematic diagram illustrating the cloning of a PCR product having non-complementary nucleotide overhang into a vector fragment having non-complementary nucleotide overhang. In this diagram, ● and ◆ are base pairs which can be paired complementarily.
Figure 2:
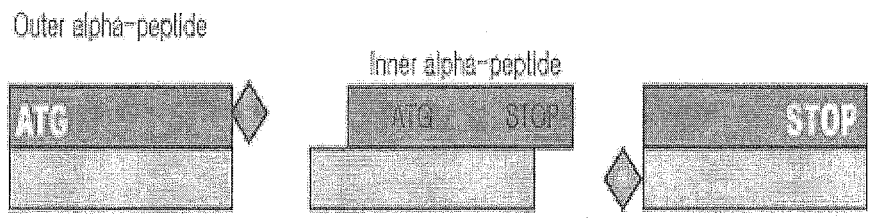
FIG. 2 is a schematic diagram illustrating the factors considered for the design of two alpha-peptide sequences necessary for the PCR product cloning vector designed according to the method of the present invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

The preparation of a parental vector is described in Example 1. The production of a PCR product cloning vector fragment having a non-complementary unpaired single overhang at the end of the sequence using the parental vector prepared in Example 1 and a restriction enzyme generating overhang in the restriction enzyme recognition site is described in Example 2. In Example 2, the restriction enzyme Xcm I forming non-complementary unpaired single overhang in the recognition site was used, but not always limited thereto and any one or a combined restriction enzyme forming non-complementary unpaired single overhang can be used. The cloning and transformation using the PCR product cloning vector having non-complementary unpaired single overhang prepared in Example 2 are described in Example 3. In Example 3, a vector fragment prepared from a parental vector but designed to be not like the one prepared by the method of the present invention and a vector fragment prepared from a parental vector according to the method of the present invention were synthesized. Chloramphenicol acetyl CoA transferase (CAT) gene was used as a target gene for cloning herein but this is only an example of application and cannot limit the present invention thereto. In fact, any gene that can be amplified by PCR can be a target. In a preferred embodiment of the present invention, one type of alpha-peptide gene sequence is described but this is only an example of various possible alpha-peptide sequences and thus the present invention is not limited thereto. In fact, a modified alpha-peptide sequence can also be used as long as its original functions are maintained.

Example 1

Preparation of a Parental Vector for the Production of a PCR Product Cloning Vector Containing Overhang Ends A parental vector used for the production of a PCR product cloning vector has to contain basic but necessary factors of a general vector. The said factors are exemplified by antibiotic resistant gene and replication origin, etc. To accomplish the present invention, a sequence having genetic information of alpha-peptide and a promoter sequence involved in the expression of the sequence are also required, in addition to the above factors, to express alpha-peptide for blue/white colony selection. And at least two restriction enzyme recognition sequences used for generating overhang ends has to be located in the alpha-peptide gene sequence. The restriction enzyme selected to generate overhang ends can be united or can be combined differently. If the restriction enzymes are different, restriction enzyme recognition sequences are obviously different. In general, the whole sequence of restriction enzyme recognition sequence is determined and no exception is accepted in most cases. Some parts of restriction enzyme recognition sequence cannot be modified, but the rest of the sequence can be modified. So, if the same restriction enzymes are used, restriction enzyme recognition sequences can be same or different in acceptable range. The restriction enzyme recognition sequence used in producing overhang ends is preferably included in the inside of alpha-peptide gene sequence. In the case of alpha-peptide gene, some modifications are allowed in the front sequence corresponding to alpha-peptide. Based on that, diverse restriction enzyme recognition sequences may be located in the front sequence corresponding to alpha-peptide. When a restriction enzyme recognition sequence used for producing overhang ends is located in the inside of alpha-peptide gene sequence, additional restriction enzyme sequences that make up a multi-cloning site (MCS) can be also inserted together. At this time, the additionally inserted restriction enzyme recognition sequences have to be assembled in the region which is not supposed to be cut off by a restriction enzyme that is the outer restriction enzyme recognition site for producing overhang ends, in order for that region to play as the region for MCS.

Figure 3:
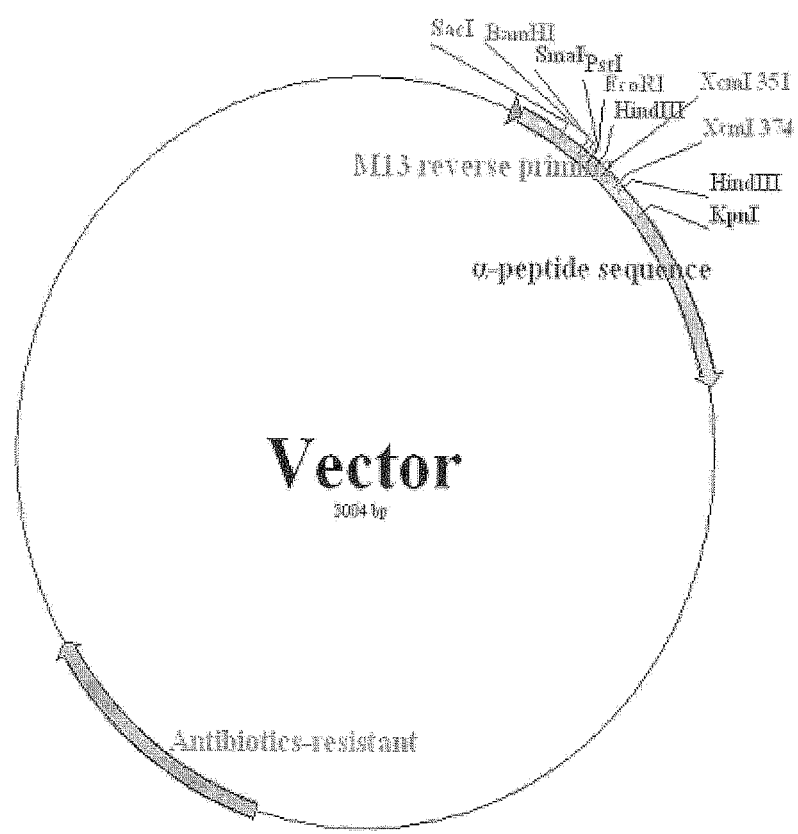
FIG. 3 is a schematic diagram illustrating the insertion of a short sequence in between restriction enzyme recognition sequences of a parental vector that is the starting vector for the production of a PCR product cloning vector.
Figure 4:
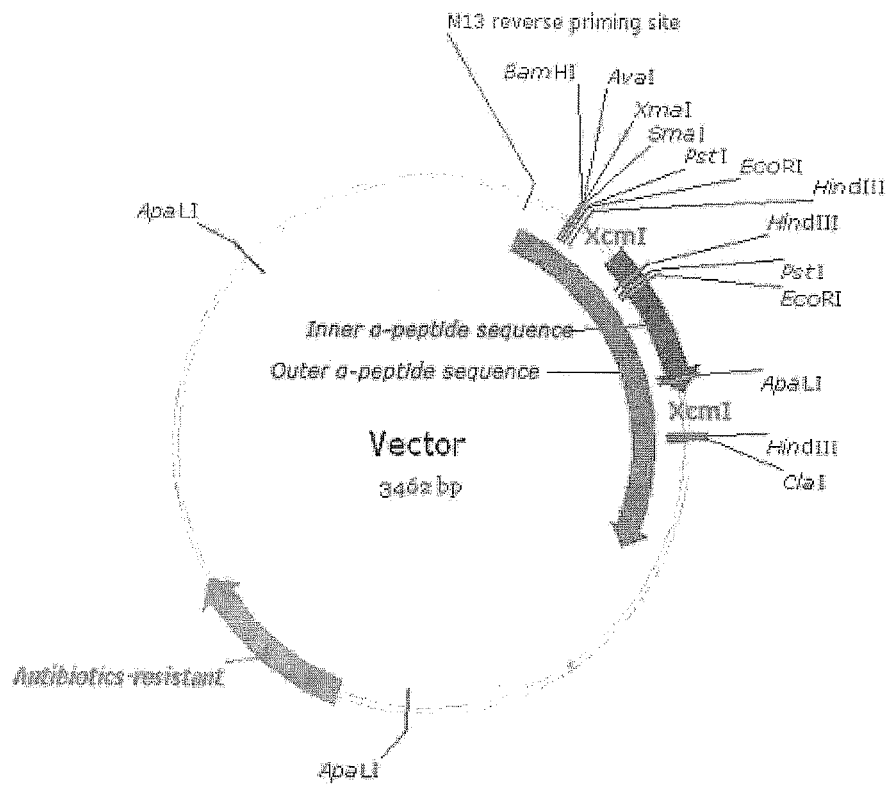
FIG. 4 is a schematic diagram illustrating the insertion of a rather long sequence containing another alpha-peptide sequence in between restriction enzyme recognition sequences of a parental vector that is the starting vector for the production of a PCR product cloning vector.
Figure 5:
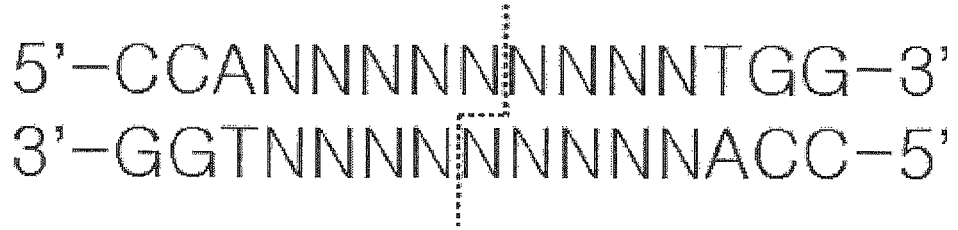
FIG. 5 is a schematic diagram illustrating the restriction enzyme Xcm I recognition sequence and digestion pattern by the same, in which Xcm I recognition sequence is composed of 15 nucleotides in total and the $5^{th}$ nucleotide residue after the first CCA is cleaved. That is, Xcm I recognizes the first CCA and the last TGG only among the 15 nucleotides and it does not matter what nucleotides are there in between as long as there are 9 nucleotides between CCA and TGG.
Figure 6:
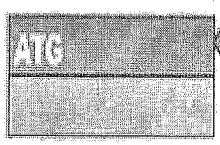
FIG. 6 is a schematic diagram illustrating the alpha-peptide gene sequence of the parental vector (parental vector 1) in which a short sequence (GCGGCCGC) is inserted in between restriction enzyme recognition sequences used for generating non-complementary unpaired single overhang.
Figure 6:
Figure 6:
Figure 7:
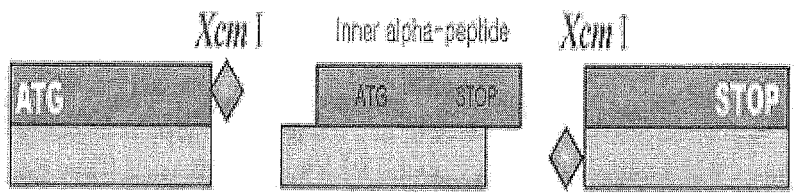
FIG. 7 is a schematic diagram illustrating the alpha-peptide sequence of the parental vector (parental vector 2) in which a rather long sequence containing another alpha-peptide sequence is inserted in between restriction enzyme recognition sequences used for generating non-complementary unpaired single overhang.

In this invention, an additional sequence composed of inner alpha-peptide sequence and the sequence related to the expression of inner alpha-peptide have to be inserted in between restriction enzyme recognition sequences used for producing overhang ends, which present in the outer alpha-peptide sequence. FIGS. 3 and 4 illustrate respectively the parental vector designed and constructed not by the method of the present invention but by the conventional method and the parental vector prepared by the method of the present invention. In the vector of FIG. 3, a short sequence (GCCGGCCGC) which is similar to the conventional one, is inserted in between two restriction enzyme recognition sequences for producing overhang ends. In the vector of FIG. 4, a rather long sequence (represented by SEQ. ID. NO: 2) containing the inner alpha-peptide sequence is inserted in between two restriction enzyme recognition sequences for producing overhang ends. In this example, the restriction enzyme selected to generate overhang ends is Xcm I. As explained hereinbefore, instead of Xcm I, another restriction enzyme or a combined enzyme composed of several restriction enzymes can be also used. Such application is well understood by those in the art, so that explanations are not given herein. Xcm I recognition sequence and cleavage site are shown in FIG. 5. In this example, two parental vectors are prepared. A short sequence (GCGGCCGC) is inserted in between restriction enzyme recognition sequences used for producing overhang ends (parental vector 1) and a rather long sequence containing another alpha-peptide is inserted in between restriction enzyme recognition sequences used for producing overhang ends (parental vector 2). The parental vector 1 is prepared not by the method of the present invention but by the conventional method to investigate the effect of the present invention. In the parental vector 1, gene sequence of alpha-peptide is represented by SEQ. ID. NO: 3, while gene sequence of alpha-peptide is represented by SEQ. ID. NO: 4 in the parental vector 2. Schematic diagrams illustrating those parental vectors are shown in FIG. 6 (parental vector 1) and in FIG. 7 (parental vector 2). The alpha peptide gene sequence in this example is only an example selected among many acceptable alpha-peptide gene sequences. When a parental vector is treated with Xcm I, a part of alpha-peptide gene sequence is eliminated to produce a vector fragment having non-complementary unpaired single overhang. When two alpha-peptide sequences are included in a parental vector, the inner alpha-peptide sequence is completely eliminated in this step. In either case, the remaining vector fragment contains alpha-peptide gene sequence divided in two portions at both ends. The parental vectors designed and constructed in this example can be mass-produced by transformation and isolated by the conventional plasmid purification method as described hereinbefore.

Example 2

Production of a Linearized Vector Fragment Containing Overhangs at Both Ends by Treating a Parental Vector with a Restriction Enzyme Capable of Generating Overhang Ends To produce a PCR product cloning vector having overhang ends, the parental vectors obtained in Example 1 were treated with Xcm I at 37° C. for 16 hours. Xcm I treatment was carried out 100 μl-scale under the following conditions but the volume and the conditions for the Xcm I treatment can be modified by those in the art. However, it is more preferred and convenient to follow the manufacturer's instructions. The restriction enzyme reaction mixture was composed of 1× restriction enzyme buffer (New England Biolabs; 10 mM Tris-HCl (pH7.5), 10 mM $MgCl_2$, 1 mM dithiothreitol (DTT), 50 mM NaCl), 20 μg of a parental vector, 50 U Xcm I (New England Biolabs), and 0.01% bovine serum albumin (BSA). In this Xcm I treatment, it is preferred to digest the parental vector as perfectly as possible. If the amount of a parental vector added to Xcm I treatment is too much or the amount of Xcm I is too less, the parental vector could be digest incompletely. Therefore, it is important to determine the amount ratio of the parent vector to Xcm I to digest the parental vector completely. According to what the present inventors confirmed, the preferable concentration of a parental vector was 0.2 μg/μl and the concentration of Xcm I was at least 0.5 U/μl. However, the said concentrations could be adjusted more or less, which did not significantly affect the efficiency of Xcm I treatment. In general, when Xcm I is added at the concentration of at least 2.5 unit per 1 μg of a parental vector, a linearized vector fragment having overhang ends can be produced without any difficulty. The addition of BSA increased the efficiency of Xcm I treatment to some degree, but not always necessary. The linearized vector fragment obtained by the treatment of Xcm I was recovered by gel-elution. Gel-elution is a method to recover a specific sized DNA molecule separated by agarose gel electrophoresis. Diverse products for gel-elution have been commercialized already. Recovering DNA by gel-elution is well known to those in the art, so that explanations are not given herein. To recover a linearized vector fragment, chromatography and alcohol precipitation can also be used instead of gel-elution.

The above result is obtained by using the parental vector 2 designed and constructed by the method of the present invention. The parental vector 1 designed and constructed not by the method of the present invention, intentionally to compare and investigate the effect of the present invention, but by the conventional way was not completely digested because the distance between two restriction enzyme recognition sites was too close, suggesting that low digestion efficiency. Besides, it was also very difficult to distinguish those fragments completely digested from those incompletely digested on agarose gel by electrophoresis, indicating that recovering of effective vector fragments was almost impossible. The decrease of digestion efficiency by too close distance between restriction enzyme recognition sites was indirectly confirmed by investigation of transformation using the vector fragments prepared by equal amount of the parental vector 1 and the parental vector 2.

Precisely, transformation was respectively performed with the restriction enzyme treatment mixtures prepared from equal amount of each parental vector without ligation. E. coli DH5α was transformed by the conventional method. After transformation, the transformed E. coli was spread on plate medium containing antibiotics. Same conditions were applied to the parental vector 1 and to the parental vector 2. The results are as follows. The following results present mean values of three independent experiments and error of each experiment is less than 10%.

TABLE 1

|  | With restriction enzyme treated mixture of parental vector 1 (conventional method) | With restriction enzyme treated mixture of parental vector 2 (method of the present invention) |
| --- | --- | --- |
| Number of colony | 252 | 33 |

As a result, many colonies were generated when the parental vector 1 was used, while the number of colonies was significantly reduced when the parental vector 2 was used. This result indicates that the restriction enzyme treatment mixture using the parental vector 2 contains far less incompletely digested vector fragments (or intact forms of the parental vector), compared with the restriction enzyme treatment mixture using the parental vector 1. This result also suggests that the insertion of an additional gene sequence containing another alpha-peptide sequence in between two restriction enzyme recognition sequences selected for generating overhang ends is effective in increasing the efficiency of the restriction enzyme treatment.

Example 3

Cloning and Transformation Using the PCR Product Cloning Vector Having Overhang Ends Cloning and transformation using the vector fragment containing non-complementary unpaired single overhang produced in Example 2 were performed as follows. First, a PCR product for cloning was prepared with CAT gene as a model gene. PCR was performed using the plasmid containing CAT gene sequence, pK7-CAT (Kim, D. M. et al., Eur. J. Biochem. 239, 881, 1996) as a template. Primers represented by SEQ.

ID. NO: 5 (5'-ATGGAGAAAAAAATCACTGGATATACA-3') and NO: 6 (5'-TTACGCCCCGCCCTGCCACTCATCG-CAG-3') were prepared by oligonucleotide synthesis and used in PCR of CAT. As a result, the amplified product of CAT gene was obtained. At this time, 50 µl of PCR reaction mixture comprising 5 µl of 10×PCR buffer (Intron Biotechnology), 5 µl of 25 mM dNTP mixture, 10 pmol of each primer, 2.5 U Taq DNA polymerase, and 10 ng of template was used. PCR was performed as follows: at 94° C. for 1 minutes, at 52° C. for 45 seconds and at 72° C. for 1 minute (30 cycles) and 72° C. for 5 minutes. The PCR product of CAT gene was electrophoresed, and recovered by gel-elution. The PCR product can be purified by phenol extraction/ethanol precipitation or the commercial PCR purification kit as well. But, it is preferred to purify the PCR product by gel-elution because this method facilitates the recovery of proper sized PCR products only with reducing contamination by non-specifically or wrong amplified products generated by any reason. The PCR product of CAT gene prepared hereinbefore was ligated to the linearized PCR product cloning vector fragment produced in Example 2 by ligation using ligase. The linearized PCR product cloning vector fragments used in this example were those produced by the method of the present invention (vector fragment produced from the parental vector 2) and by the conventional method (vector fragment produced from the parental vector 1: control vector fragment). Those vector fragments were also purified by gel-elution.

The ligation buffer for ligase reaction was provided by Intron Biotechnology (30 mM Tris-HCl (pH7.5), 0.1 mM ATP, 10 mM magnesium chloride, 10 mM dithiothreitol). Ligation was carried out at 16° C. for overnight to ligate the PCR product of CAT to the vector fragment. Then, *E. coli* DH5α was transformed directly with the ligation mixture without purification. After transformation, *E. coli* was spread on plate medium containing antibiotics, which was also pretreated with IPTG and X-Gal. The transformed *E. coli* was then incubated for overnight to form colonies. Colors of colonies were observed and only white colonies were selected. The selected colonies were inoculated in a liquid medium containing a proper antibiotic, followed by shaking incubation. Massive amount of the cloning product containing the PCR product was isolated by the conventional plasmid extraction method.

To investigate if the plasmid obtained from the culture of white colony was the proper cloning product, PCR analysis and restriction enzyme mapping was performed with the isolated plasmid. PCR for PCR analysis was performed by the same manner as described above for the preparation of the PCR product of CAT. After PCR, 1 µl of the PCR reaction mixture was taken, followed by electrophoresis. After electrophoresis, DNA was stained by the conventional method, followed by UV irradiation to investigate the PCR product. If the proper sized PCR product was generated, cloning was successful. But if the proper sized PCR product was not generated, cloning was unsuccessful. For restriction enzyme mapping, the isolated plasmid was treated with proper restriction enzymes and the sizes of the released DNA fragments were measured to confirm whether the cloning was successfully performed. The proper restriction enzymes for this restriction enzyme mapping were selected among restriction enzymes from each side of the outside of Xcm I recognition sequence, that is, from outside of the cloned gene. The results are as follows.

TABLE 2

| | | Number of colony | | Ratio of colonies containing a cloning product in |
|---|---|---|---|---|
| | Investigation method | Blue colony | White colony | white colonies (%) |
| Conventional method (vector fragment produced from parental vector 1) | PCR analysis | 273 | 8 | 100 |
| | | 268 | 10 | 90 |
| | | 259 | 11 | 90 |
| | Restriction enzyme mapping | 264 | 15 | 93 |
| | | 271 | 10 | 90 |
| | | 268 | 12 | 91 |
| Method of the present invention (vector fragment produced from parental vector 2) | PCR analysis | 75 | 300 | 96 |
| | | 62 | 290 | 100 |
| | | 88 | 285 | 96 |
| | Restriction enzyme mapping | 61 | 278 | 100 |
| | | 69 | 302 | 100 |
| | | 81 | 262 | 98 |

As a result, when the vector fragment produced by using the parental vector 1 was used for cloning, too many blue colonies were generated, indicating the ratio of white colonies in the total colonies was comparatively low. In both cases of using the vector fragment produced by using the parental vector 1 and using the vector fragment produced by using the parental vector 2, most of white colonies were effective colonies, which are colonies having a proper cloning product, as confirmed by examining ratio of colonies containing a cloning product in white colonies. But, the cloning efficiency of using the vector fragment produced by using the parental vector 1 was lower than that of using the vector fragment produced by using the parental vector 2. This was resulted from incomplete vector digestion.

From the above results, it was confirmed that the PCR product cloning vector fragment of the present invention was working properly and further the method of the present invention using the PCR product cloning vector fragment facilitated more effective cloning than the conventional method. Even if a long sequence is inserted in between restriction enzyme recognition sequences selected to generate overhang ends on a parental vector to increase vector fragment production efficiency, a transformant having the parental vector is still appeared as a blue colony in blue/white colony selection, indicating that the method of the present invention overcomes the problem of the conventional method in blue/white colony selection such that a transformant having the parental vector may appear as a white colony with making selection difficult. This was confirmed by that ratio of colonies containing a cloning product in white colonies was maintained unchanged. Therefore, the PCR product cloning vector produced by the method of the present invention can improve cloning efficiency and still be effective in blue/white colony selection, precisely effective colonies containing a cloning product can be sorted out by selecting white colonies only.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of making a linearized double-stranded DNA vector fragment for direct cloning of a polymerase chain reaction (PCR) product by Xcm I restriction enzyme treatment of a circular parental alpha-peptide gene sequence containing vector comprising the nucleotide sequence of SEQ ID NO:4 comprising two Xcm I restriction enzyme recognition sequences, wherein Xcm I restriction enzyme treatment generates a double-stranded DNA vector fragment having non-complementary unpaired single overhang ends in the recognition site in different strands of the double-stranded DNA structure.

2. The method of claim 1, wherein the nucleotide sequence of SEQ ID NO:4 is generated by inserting into a parental vector a first alpha-peptide gene sequence of SEQ ID NO: 1, wherein said sequence comprises two Xcm I restriction enzyme recognition sequences, wherein a second alpha-peptide gene sequence of SEQ ID NO: 2 is inserted in between Xcm I restriction enzyme recognition sequences present in the first alpha-peptide sequence.

3. A linearized PCR product cloning vector fragment made by the method of claim 1, wherein the linearized PCR product cloning vector fragment comprises a double-stranded DNA structure, wherein both ends of the linearized PCR product cloning vector fragment comprise a non-complementary unpaired single overhang, and wherein the non-complementary unpaired single overhangs are located in different strands of the double-stranded DNA structure.

4. The PCR product cloning vector fragment of claim 3, wherein the fragment comprises SEQ ID NO: 2.

* * * * *

SEQUENCE LISTING

<160> NUMBER OF SEQ ID NOS: 6

<210> SEQ ID NO 1
<211> LENGTH: 273
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 1

| | | | | | |
|---|---|---|---|---|---|
| atgggggatc | ccaagcttct | tctagaggta | ccgcatgcga | tatcgagctc | tcccgggaat | 60 |
| tcactggccg | tcgttttaca | acgtcgtgac | tgggaaaacc | ctggcgttac | ccaacttaat | 120 |
| cgccttgcag | cacatccccc | tttcgccagc | tggcgtaata | gcgaagaggc | ccgcaccgat | 180 |
| cgcccttccc | aacagttgcg | cagcctgatc | cggctgctaa | caaagcccga | aggaagctg | 240 |
| agttggctgc | tgccaccgct | gagcaataac | tag | | | 273 |

<210> SEQ ID NO 2
<211> LENGTH: 466
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 2

| | | | | | |
|---|---|---|---|---|---|
| gcggccgctt | agctcactca | ttaggcaccc | caggctttac | actttatgct | tccggctcgt | 60 |
| atgttgtgtg | gaattgtgag | cggataacaa | tttcacacag | gaaacagcta | tgaccatgat | 120 |
| tacgccaagc | ttgcatgcct | gcagtctaga | ccggaattca | ctggccgtcg | ttttacaacg | 180 |
| tcgtgactgg | gaaaaccctg | gcgttaccca | acttaatcgc | cttgcagcac | atccccttt | 240 |
| cgccagctgg | cgtaatagcg | aagaggcccg | caccgatcgc | ccttcccaac | agttgcgcag | 300 |
| cctgaatggc | gaatggcgcc | tgatgcggta | ttttctcctt | acgcatctgt | gcggtatttc | 360 |
| acaccggtgc | actctcagta | caatctgctc | tgatgccgca | tagttaagcc | agccccgaca | 420 |
| cccgccaaca | cccgctgacg | cgccctgacg | ggcttgtcgc | ggccgc | | 466 |

<210> SEQ ID NO 3
<211> LENGTH: 450
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 3

| | | | | | |
|---|---|---|---|---|---|
| atgaccatga | ttacgccaag | ctcgaaatta | accctcacta | aagggaacaa | aagctggagc | 60 |
| tccaccgcgg | tggcggccgc | tctagaacta | gtggatcccc | cgggctgcag | gaattcgata | 120 |
| tcaagcttcc | agagctcagt | tgggcggccg | cccagacgag | acgtggcaag | cttatcgata | 180 |
| ccgtcgacct | tcaggggggg | cccggtaccc | aattcgccct | atagtgagtc | gtattacaat | 240 |
| tcactggccg | tcgttttaca | acgtcgtgac | tgggaaaacc | ctggcgttac | ccaacttaat | 300 |
| cgccttgcag | cacatccccc | tttcgccagc | tggcgtaata | gcgaagaggc | ccgcaccgat | 360 |
| cgcccttccc | aacagttgcg | cagcctgaat | ggcgaatggc | aaattgtaag | cgttaatatt | 420 |
| ttgttaaaat | tcgcgttaaa | ttttttgttaa | | | | 450 |

<210> SEQ ID NO 4

<211> LENGTH: 908
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 4

| | | | | | |
|---|---|---|---|---|---|
| atgaccatga | ttacgccaag | ctcgaaatta | accctcacta | aagggaacaa | aagctggagc | 60 |
| tccaccgcgg | tggcggccgc | tctagaacta | gtggatcccc | cgggctgcag | gaattcgata | 120 |
| tcaagcttcc | agagctcagt | tgggcggccg | cttagctcac | tcattaggca | ccccaggctt | 180 |
| tacactttat | gcttccggct | cgtatgttgt | gtggaattgt | gagcggataa | caatttcaca | 240 |
| caggaaacag | ctatgaccat | gattacgcca | agcttgcatg | cctgcagtct | agaccggaat | 300 |
| tcactggccg | tcgttttaca | acgtcgtgac | tgggaaaacc | ctggcgttac | ccaacttaat | 360 |
| cgccttgcag | cacatccccc | tttcgccagc | tggcgtaata | gcgaagaggc | ccgcaccgat | 420 |
| cgcccttccc | aacagttgcg | cagcctgaat | ggcgaatggc | gcctgatgcg | gtattttctc | 480 |
| cttacgcatc | tgtgcggtat | ttcacaccgg | tgcactctca | gtacaatctg | ctctgatgcc | 540 |
| gcatagttaa | gccagccccg | acacccgcca | acacccgctg | acgcgccctg | acgggcttgt | 600 |
| cgcggccgcc | cagacgagac | gtggcaagct | tatcgatacc | gtcgaccttc | aggggggggcc | 660 |
| cggtacccaa | ttcgccctat | agtgagtcgt | attacaattc | actggccgtc | gttttacaac | 720 |
| gtcgtgactg | ggaaaaccct | ggcgttaccc | aacttaatcg | ccttgcagca | catccccctt | 780 |
| tcgccagctg | gcgtaatagc | gaagaggccc | gcaccgatcg | cccttcccaa | cagttgcgca | 840 |
| gcctgaatgg | cgaatggcaa | attgtaagcg | ttaatatttt | gttaaaattc | gcgttaaatt | 900 |
| tttgttaa | | | | | | 908 |

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 5
atggagaaaa aaatcactgg atataca     27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 6
ttacgccccg ccctgccact catcgcag     28